(12) United States Patent
Gou et al.

(10) Patent No.: US 11,009,442 B2
(45) Date of Patent: May 18, 2021

(54) PLATE HOLDER FOR SIMULATING FLOWING OF MULTIPHASE FLUIDS IN FRACTURES AND AN OPERATING METHOD THEREOF

(71) Applicant: SOUTHWEST PETROLEUM UNIVERSITY, Chengdu (CN)

(72) Inventors: Bo Gou, Chengdu (CN); Jianchun Guo, Chengdu (CN); Chi Chen, Chengdu (CN); Xiao Li, Chengdu (CN); Chao Liu, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 0 days.

(21) Appl. No.: 16/878,637

(22) Filed: May 20, 2020

(65) Prior Publication Data
US 2020/0284712 A1 Sep. 10, 2020

(30) Foreign Application Priority Data
Feb. 26, 2020 (CN) .......................... 2020101199249

(51) Int. Cl.
| | | |
|---|---|---|
| G01N 15/08 | (2006.01) | |
| G01N 33/24 | (2006.01) | |
| E21B 49/02 | (2006.01) | |
| E21B 43/26 | (2006.01) | |

(52) U.S. Cl.
CPC ......... *G01N 15/0826* (2013.01); *E21B 49/02* (2013.01); *G01N 15/0806* (2013.01); *G01N 33/24* (2013.01); *E21B 43/26* (2013.01)

(58) Field of Classification Search
CPC .... G01N 15/00; G01N 15/08; G01N 15/0806; G01N 15/0826; G01N 33/24; E21B 43/26; E21B 49/02
See application file for complete search history.

(56) References Cited

FOREIGN PATENT DOCUMENTS

| CN | 105784456 A | * | 7/2016 | ............ G01N 1/36 |
|---|---|---|---|---|
| CN | 206035473 U | * | 3/2017 | ............ E21B 47/00 |
| CN | 109374859 A | | 2/2019 | |
| CN | 201811221416 A | * | 2/2019 | ............ G01N 33/24 |
| CN | 210295637 U | * | 4/2020 | ............ G09B 25/02 |

\* cited by examiner

*Primary Examiner* — Nguyen Q. Ha (57) ABSTRACT

The invention discloses a plate holder for simulating flowing of multiphase fluids in fractures, comprising a rectangular box, provided with a fluid inlet and a fluid outlet at the left and right sides respectively, the fluid inlet is connected to a piston at the fluid inlet, the fluid outlet is connected to a piston at the fluid outlet, an internal flow channel of the piston is arranged as a flared guide groove, and the cavity between the pistons is a rock plate cavity; a pair of horizontally-overlapped rectangular rock plates are installed in the rock plate cavity, four sides parallel to the length direction of the rock plate are completely attached and covered with rubber, the outer side of the rubber is covered with steel plate, fastening screws are installed vertically on the four sides of the box that are directly opposite to the steel plate.

9 Claims, 6 Drawing Sheets

PLATE HOLDER FOR SIMULATING FLOWING OF MULTIPHASE FLUIDS IN FRACTURES AND AN OPERATING METHOD THEREOF

BACKGROUND OF THE INVENTION

Field of the Invention

The present invention relates to a plate holder for simulating flowing of multiphase fluids in fractures and an operating method thereof, in particular to a plate holder device for simulating flowing of multiphase fluids in underground rock fractures and an operating method thereof in the field of engineering.

Description of Related Art

Multiphase flow in underground rock fractures is common in various engineering fields involving underground rocks. For example, gas-liquid flow of $CO_2$ and formation water in fractures (Zhang Zhixiong, Xie Jian, Qi Jihong, et al. Numerical simulation of $CO_2$ leakage along faults from geologic carbon dioxide sequestration [J]. Hydrogeology and Engineering Geology, 2018 45 (02): 109)), gas-liquid flow of fracturing fluid and $CO_2$ in hydraulic fractures during $CO_2$ foam fracturing in hydrocarbon reservoir (Liu Tongyi, Chen Guangjie, Tan Kun. Application of $CO_2$ foam fracturing technology in deep gas reservoirs [J]. Natural Gas Industry, 2007 27 (8): 88-90)), flow and reaction of mixture of acid fluid and supercritical $CO_2$ in the hydraulic fracture during $CO_2$ injection in the acid fracturing in hydrocarbon reservoir (Sanchez Bernal, M., Tate, J., Idris, M., Soriano, J. E., Lopez, A. E., & Fatkhutdinov, D., Acid Fracturing Tight Gas Carbonates Reservoirs Using $CO_2$ to Assist Stimulation Fluids: An Alternative to Less Water Consumption while Maintaining Productivity [C]. SPE 172913-MS), and gas-liquid-solid flow of natural gas, formation water, fracturing fluid and broken rock particles on the fracture wall in the process of gas well production (Xu Tuotuo. Research on gas-liquid-solid flow mechanism and sand-carrying law of water-producing gas wells [M]. China University of Petroleum (East China), 2016).

The multiphase flow in fractures is obviously different from the single-phase flow. Experimental simulation of multiphase flow in fractures is the most direct method to understand the mechanism of multiphase flow in underground rock fractures, which can provide direct guidance for related engineering design. The plate holder is the core component for experimental simulation of multiphase flow. The patent (Application No.: 201711120544.1) provides a triaxial core holder for simulating the gas-water flow in fractures of shale reservoirs. However, the holder is mainly used to hold plunger-shaped shale core sample. It can simulate the gas-water flow in small-scale shale fractures, but it is difficult to simulate the flow reaction of multiphase fluid in carbonate fractures. The patent (Application No.: 201010203373.0) provides a plate holder for simulating flowing reaction of acid fluid in fractures. However, the plate holder and other similar holders existing in the prior art have the following disadvantages. (1) The cavity of the holder is in the shape of a long circular arc cylinder. It is required to load the rock sample from the top and bottom of the cylinder cavity respectively, and then install the two upper and lower long circular arc cylinder pistons. Each piston is provided with only one stage seal ring for sealing. The experiment shows that the device is very easy to cause fluid leakage when simulating the reaction of gas-liquid flow, and there is a serious potential safety hazard. (2) A gasket is used to set the fracture width for the rock sample and then the rock sample is loaded into the holder. However, in the loading of the rock samples, the fracture width is greatly affected by human factors, so it is difficult to accurately reach the experimental preset value. (3) The rock sample in the plate holder is sealed by means of rigid contact sealing with the rock sample. The epoxy resin sealant on the surface of rock plate is prone to serious expansion when encountering highly corrosive multiphase fluids (such as acid and $CO_2$), which will cause the corrosive fluid to leak from the rock sample.

Therefore, it is urgent to develop and design a multifunctional plate holder for simulating flowing of multiphase fluids in fractures, so as to simulate the physical process of multiphase flow in the fractures of rock samples, and simulate the chemical reaction process between the multiphase fluid in the fractures of rock samples and the rocks on the fracture wall.

SUMMARY OF THE INVENTION

The purpose of the present invention is to provide a multi-functional plate holder for simulating flowing of multiphase fluids in fractures, in view of technical defect of the prior art that the plate holder cannot be used for the simulation experiment of the highly corrosive multiphase fluid flowing in the fracture.

The technical proposal is as follows:

The plate holder for simulating flowing of multiphase fluids in fractures provided by the present invention comprises a rectangular box, which is provided with a fluid inlet and a fluid outlet at the left and right sides respectively, the fluid inlet is connected to a piston at the fluid inlet, the fluid outlet is connected to a piston at the fluid outlet, the pistons are same in shape and structure, an internal flow channel of the piston is arranged as a flared guide groove, the flared ends of the two pistons are opposite to each other, and the cavity between the pistons is a cuboid rock plate cavity. The left or right side of the body of the rectangular box is provided with a heater hole for inserting an electric heating rod.

A pair of horizontally-overlapped rectangular rock plates are installed in the rock plate cavity, a gap is left between the two rock plates to simulate the fracture width, four sides parallel to the length direction of the rock plate are completely attached and covered with rubber, the outer side of the rubber is covered with steel plate, the rock plate is completely surrounded by the steel plates on four sides. A plurality of round holes are cut in the four sides of the box that are directly opposite to the steel plate, and the fastening screws perpendicular to the sides of the box and the steel plate are installed in the round holes, and the screw end is in contact with the steel plate. The gap between the two rock plates can be changed by adjusting the fastening screws on the upper and lower sides to simulate different fracture widths. The steel plates can be pushed by adjusting the fastening screws on the front and rear sides to press the rubber for sealing the sides of the rock plate; there are at least 2 fastening screws arranged on the upper and lower sides of the body of the rectangular box, and a scale for measuring the length is provided on the upper part of the screw, with an accuracy of 1 mm. There are at least 4 fastening screws arranged on the front and rear sides; two sealing grooves are arranged at the lower part of all fastening screws, and seal rings are installed in the sealing grooves.

Preferably, a fluid inlet and a fluid outlet are arranged at the centers of the left and right sides of the box respectively, the bases are installed with hexagon socket square bolts respectively at the positions of the fluid inlet and outlet, the center of the base is provided with a fluid flow channel which is perpendicular to the side of the box, and the gap between the two plates is directly opposite to and connected with the flow channel, the outer side of the base is installed with the fluid inlet piston or the fluid outlet piston by hexagon socket square bolts, the flared end of the piston is directly opposite to and connected with the fluid channel at the base center, and the shape and size of the flared end are same with the fluid channel of the base.

Further preferably, the base is composed of a base plate and a plug which is located at one side of the base plate and is vertically connected with the base plate, the base plate and the plug are integrally formed, the plug is inserted into the fluid inlet or the fluid outlet to completely block it, the base plate is located outside the box and tightly against the side of the box, the base plate and the side of the box are fixedly connected by hexagon socket square bolts, and the outer side of the base plate is connected with the fluid inlet piston or the fluid outlet piston by hexagon socket square bolts. A seal ring is provided respectively at the contact position between the left and right sides of the rock plate and the plug, at the connection position between the left and right sides of the body of the rectangular box and the base plate, and at the connection position between the outer side of the base plate and the fluid inlet piston or the fluid outlet piston.

Preferably, the upper and lower sides of the body of the rectangular box are respectively provided with 3 fastening screws, which are located on the center line parallel to the long side of the body of the rectangular box and equally spaced. the front and rear sides of the body of the rectangular box are respectively provided with 6 fastening screws, which are arranged in two rows, 3 screws in one row and equally spaced.

The operating method of the plate holder for simulating flowing of multiphase fluids in fractures, comprising the following steps:

(1) preparing a pair of rectangular rock plate samples in line with the size of the rock plate cavity in the plate holder;

(2) placing the pair of rock plate in a horizontally-overlapped way, with a spacing $w_o$ which is greater than the fracture width w designed in the experiment, attaching rubber with the same area to the rock plate's four sides parallel to the multiphase fluid, wrapping the four sides with steel plates, and placing the wrapped rock plate horizontally in the rock plate cavity of the plate holder;

(3) installing the fastening bolts vertically on the front and rear sides and the upper and lower sides of the plate holder box, which are directly opposite to the steel plates, and rotating and pushing the fastening screws on the front and rear sides to push the steel plate to move and press the rubber to fix and seal the rock plate;

(4) rotating the fastening screws on the upper and lower sides until they comes into contact with the steel plate, recording the scale value S, and tightening the bolts until the scale is $w_o-w=S$, to make the fracture width value reaches the fracture width w designed in the experiment; and (5) using hexagon socket square bolts to fix the fluid inlet piston and the fluid outlet piston to the fluid inlet and fluid outlet of the box respectively to complete the installation of the plate holder.

Compared with the prior art, the present invention has the following beneficial effects:

(1) The plate holder is formed and machined as a whole, rather than being sealed by the upper and lower pistons, the rock samples are loaded through the multiphase fluid inlet and outlet, the four sides of the holder body are equipped with a plurality of bolts with two-stage seal rings to fix the rock sample position, and the fluid inlet piston and outlet piston at both ends of the holder are also sealed with two-stage seal ring. The above improvement measures will ensure the tightness of the holder without safety risks to the greatest extent. (2) The upper part of the fastening screw is engraved with a scale with an accuracy of 1 mm to accurately measure the tightness of the bolt, which can realize the dynamic control of the sample fracture, ensure the controllability of the fracture in the simulation of multiphase fluid flow experiment. (3) The seal ring is made of corrosion-resistant and airtight materials, to ensure the diversity of multiphase fluids which can be a combination of gas and liquid without corrosiveness, or a combination of gas and liquid with corrosiveness. (4) It can not only simulate the physical flow process of multiphase fluid in different rock materials, but also simulate the physical and chemical reactions.

Other advantages, objectives and characteristics of the present invention will be partly embodied by the following description, and partly understood by those skilled in the art through research and practice of the present invention.

BRIEF DESCRIPTION OF THE DRAWINGS

Aspects of the present invention are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DESCRIPTION OF THE PREFERRED EMBODIMENTS

In the following detailed description of the preferred embodiments of the present invention, reference is made to the accompanying drawings. It is to be understood that the preferred embodiments described herein are only used to illustrate and interpret the present invention and are not intended to limit the present invention.

As shown in FIG. 1 to FIG. 6, the plate holder for simulating flowing of multiphase fluid in the fracture provided by the present invention is a rectangular box 1, which is provided with a fluid inlet and a fluid outlet at the centers of the left and right sides of the box respectively. The bases 3 are installed with hexagon socket square bolts 2 respectively at the positions of the fluid inlet and outlet. The center of the base is provided with a fluid flow channel 4 which is perpendicular to the side of the box. Piston 5 at the fluid inlet end is mounted outside the fluid inlet base with hexagon socket square bolts. Piston 6 at the fluid outlet end is mounted outside the fluid outlet base with hexagon socket square bolts. The pistons are same in shape and structure. The internal flow channel of the piston is arranged as the flared guide groove 7. The flared ends of the two pistons are opposite to each other. The cavity between the pistons is designed as a cuboid rock plate cavity. The flared end of the piston is directly opposite to and connected with the fluid channel at the base center, and the shape and size of the flared end are same with the fluid channel of the base. At the flared ends of the pistons at the fluid inlet and outlet, the ports are connected to a plate-shaped connector 16. The connector is provided with bolt hole and integrally formed with the piston. The pistons at the fluid inlet and outlet are sealed and connected with the base by the connector 16.

A pair of horizontally-overlapped rectangular rock plates 8 is installed in the rock plate cavity, and a gap 18 is left between the two rock plates to simulate the fracture width. The gap between the two plates is directly opposite to and connected with the flow channel 4. Four sides parallel to the length direction of the rock plate are completely attached and covered with rubber 9, the outer side of the rubber is covered with steel plate 10, and the rock plate is completely surrounded by the steel plates on four sides. The body of the rectangular box is provided with a plurality of round holes on the four sides directly opposite to the steel plate. Fastening screws 11 are installed in the round holes, and kept perpendicular to the sides of the box and the targeted steel plate and tightly against the steel plates. The screw end is in contact with the steel plate. The gap between the two rock plates can be changed by adjusting the fastening screws on the upper and lower sides to simulate different fracture widths. The steel plates can be pushed by adjusting the fastening screws on the front and rear sides to press the rubber for sealing the sides of the rock plate. There are at least 2 fastening screws arranged on the upper and lower sides of the body of the rectangular box, and a scale 17 for measuring the length is provided on the upper part of the screw, with an accuracy of 1 mm. There are at least 4 fastening screws arranged on the front and rear sides. Two sealing grooves are arranged at different positions of the lower part of all fastening screws, and seal rings 12 are installed in the sealing grooves. Preferably, the upper and lower sides of the body of the rectangular box are respectively provided with 3 fastening screws, which are located on the center line parallel to the long side of the body of the rectangular box and equally spaced. The front and rear sides of the body of the rectangular box are respectively provided with 6 fastening screws, which are arranged in two rows, 3 screws in one row and equally spaced.

The left or right side of the body of the rectangular box is provided with a heater hole 13 in the flowing direction for inserting an electric heating rod.

Figure 1:
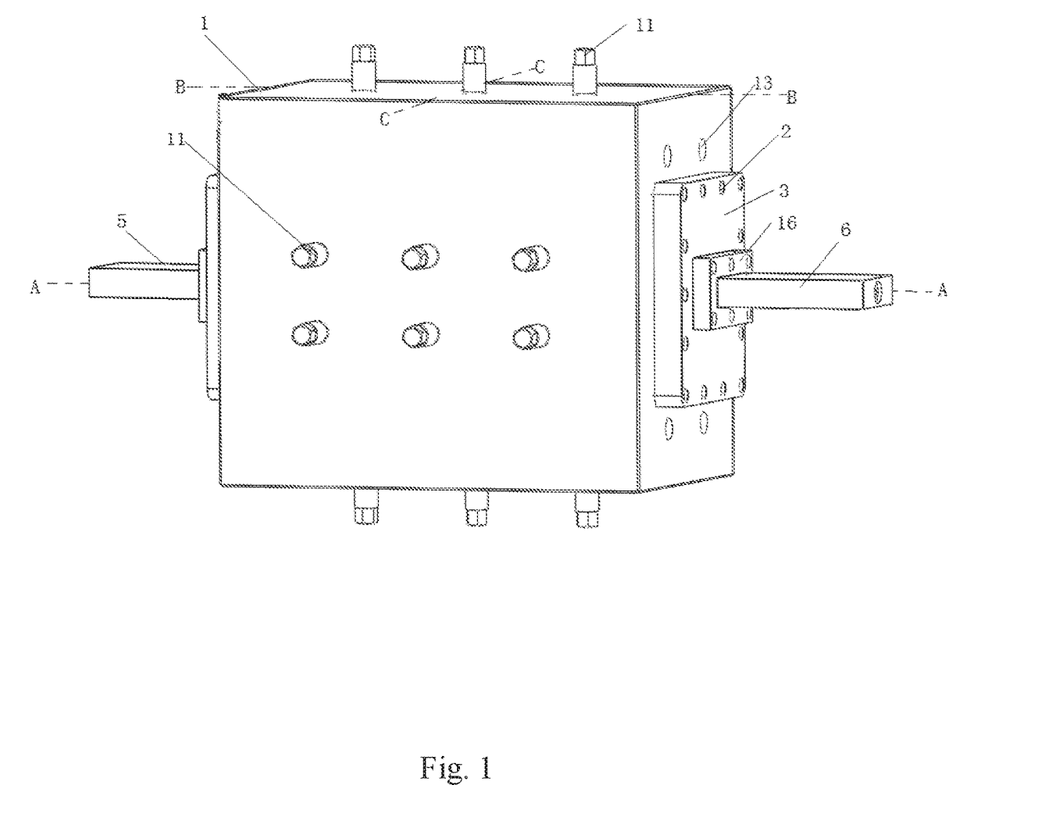
FIG. 1 is a schematic diagram of the outline structure of a plate holder for simulating flowing of multiphase fluids in fractures provided by the present invention.
Figure 2:
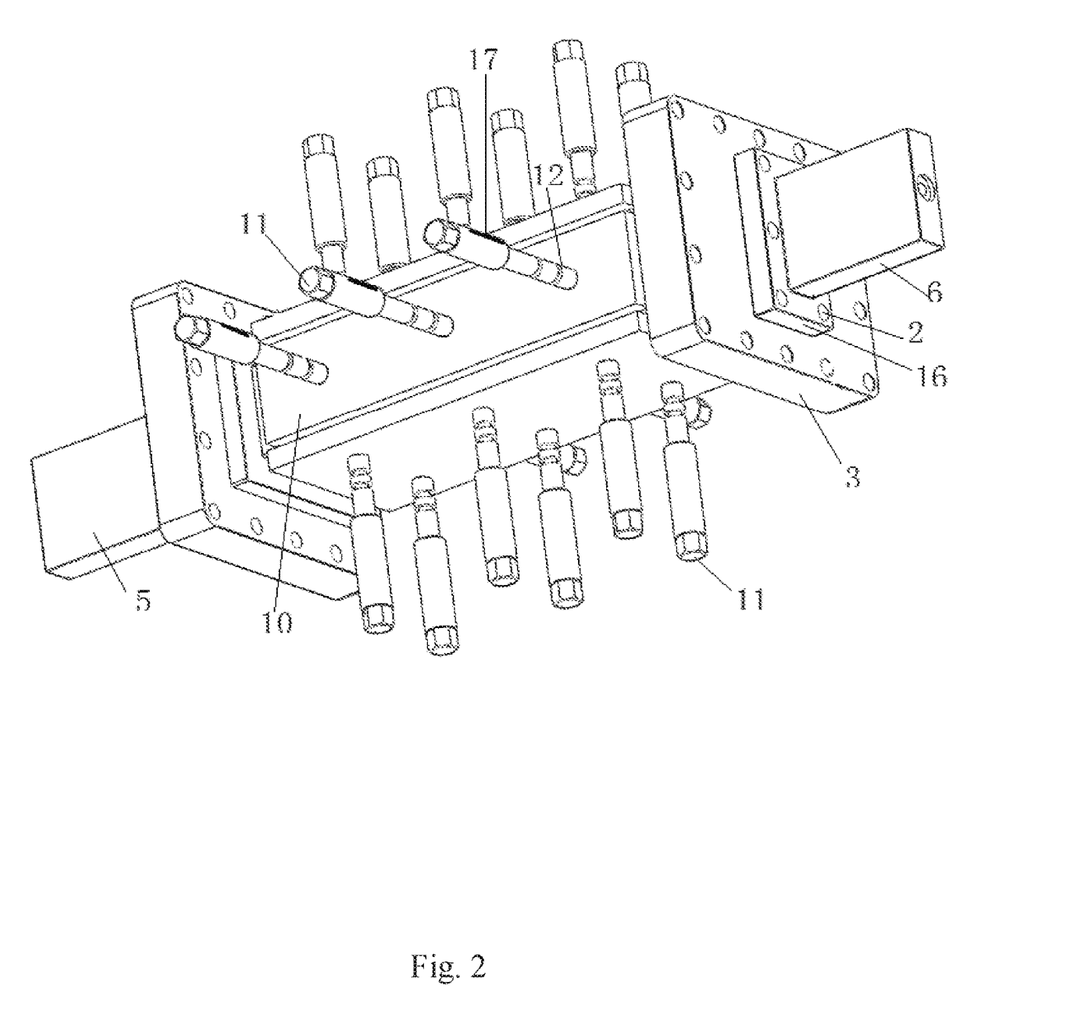
FIG. 2 is a schematic diagram of the internal structure of a plate holder for simulating flowing of multiphase fluids in fractures provided by the present invention.
Figure 3:
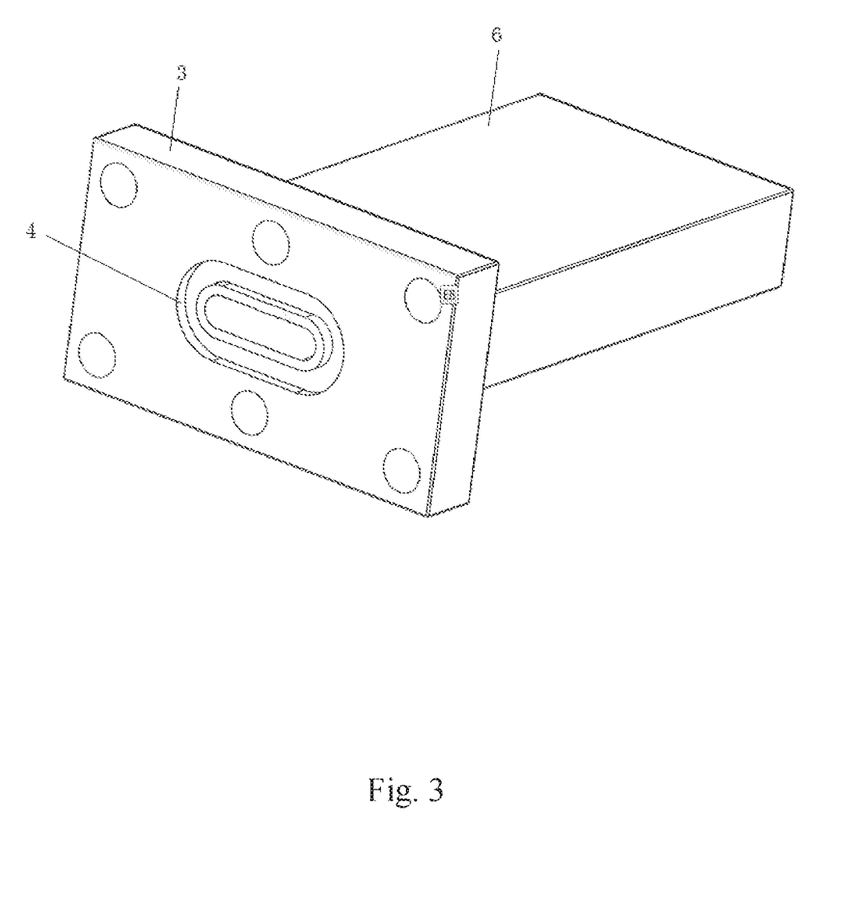
FIG. 3 is a structural diagram of piston and base at fluid outlet or inlet.
Figure 4:
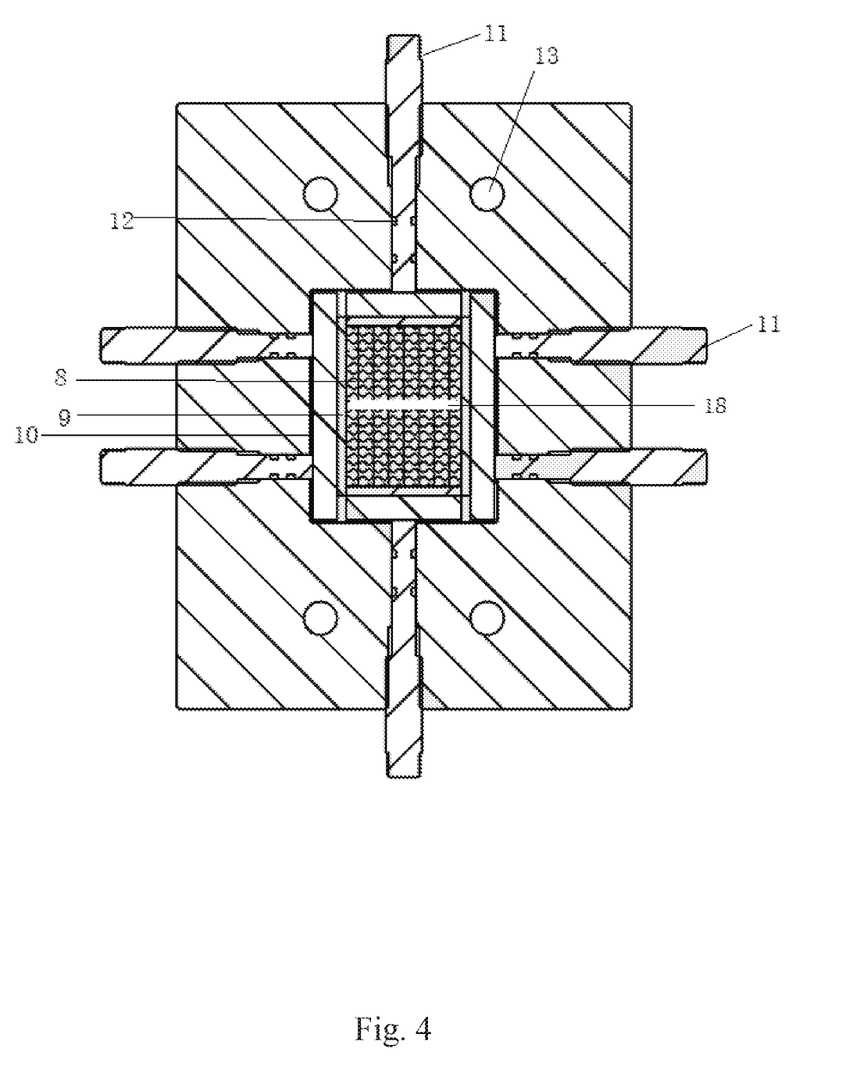
FIG. 4 is a sectional view of C-C longitudinal section of the plate holder shown in FIG. 1.
Figure 5:
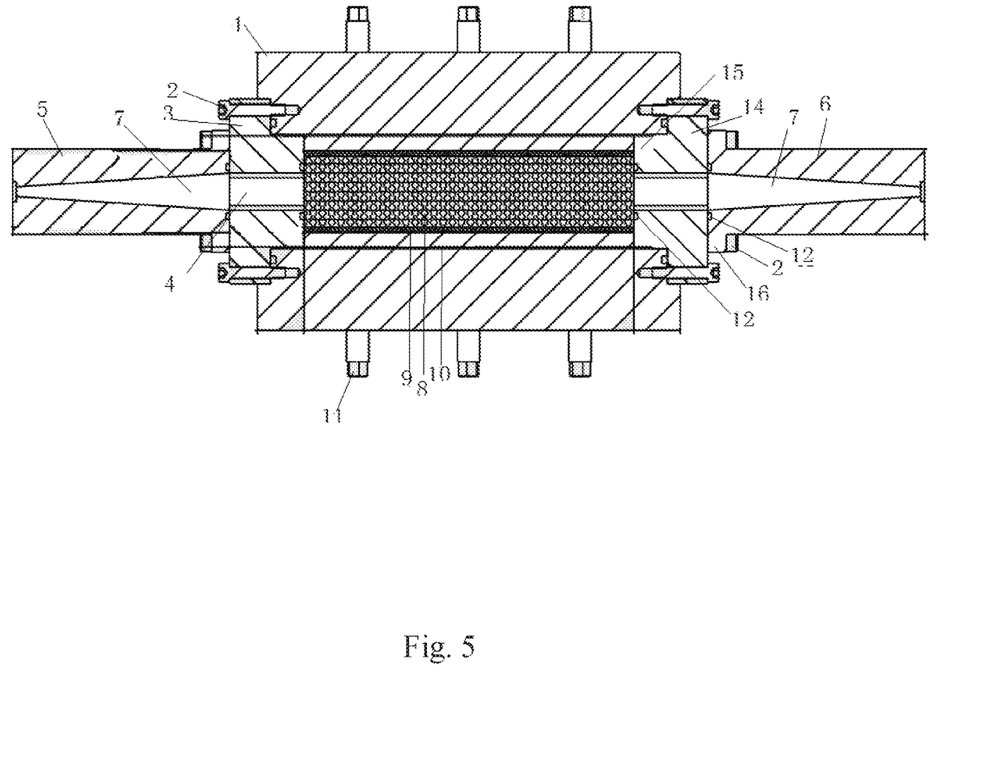
FIG. 5 is a sectional view of A-A horizontal section of the plate holder shown in FIG. 1.
Figure 6:
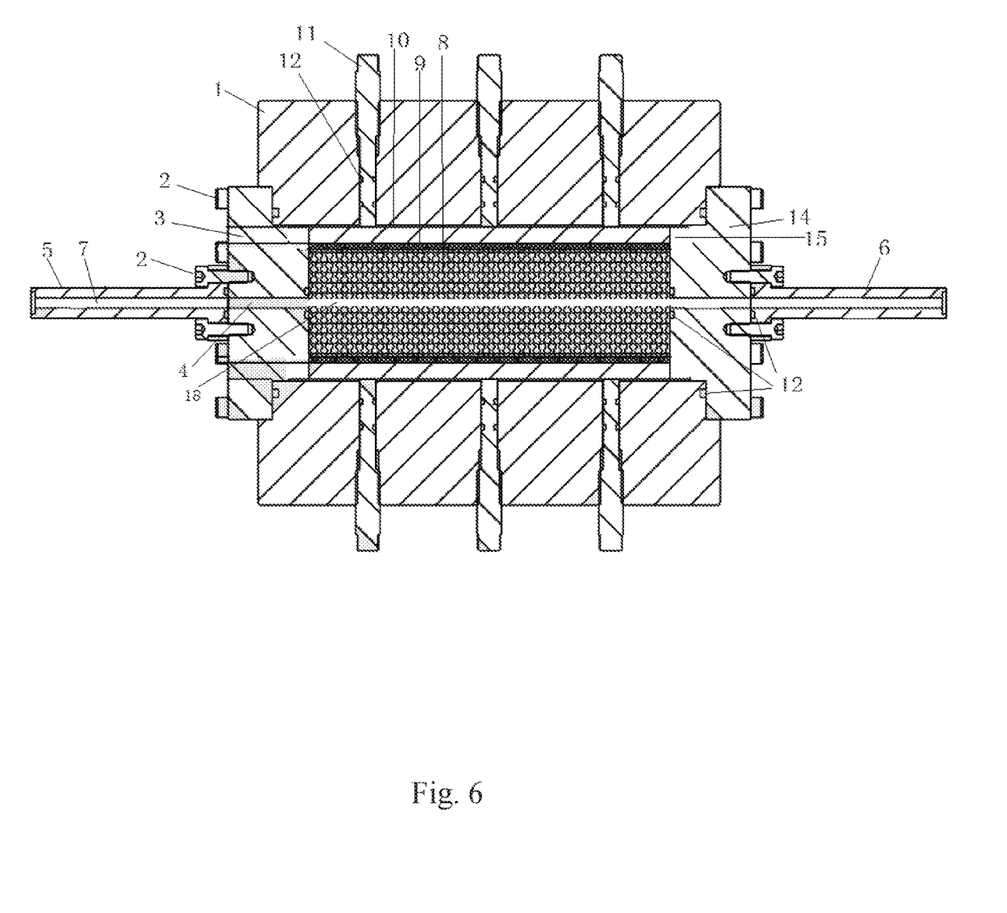
FIG. 6 is a sectional view of B-B longitudinal section of the plate holder shown in FIG. 1.

In another embodiment, the base is composed of a base plate 14 and a plug 15 which is located at one side of the base plate and is vertically connected with the base plate. The base plate and the plug are integrally formed. The plug is inserted into the fluid inlet or the fluid outlet to completely block it. The base plate is located outside the box and tightly against the side of the box. The base plate and the side of the box are fixedly connected by hexagon socket square bolts. The outer side of the base plate is connected with the fluid inlet piston or the fluid outlet piston by hexagon socket square bolts. A seal ring 12 is provided respectively at the contact position between the left and right sides of the rock plate and the plug, at the connection position between the left and right sides of the body of the rectangular box and the base plate, and at the connection position between the outer side of the base plate and the fluid inlet piston or the fluid outlet piston.

The installation method of the plate holder for simulating flowing of multiphase fluids in fractures, comprising the following steps:

(1) preparing a pair of rectangular rock plate samples in line with the size of the rock plate cavity in the plate holder;

(2) placing the pair of rock plate in a horizontally-overlapped way, with a spacing $w_o$ which is greater than the fracture width w designed in the experiment, attaching rubber with the same area to the rock plate's four sides parallel to the multiphase fluid, wrapping the four sides with steel plates, and place the wrapped rock plate horizontally in the rock plate cavity of the plate holder;

(3) installing the fastening bolts vertically on the front and rear sides and the upper and lower sides of the plate holder box, which are directly opposite to the steel plates, and rotating and pushing the fastening screws on the front and rear sides to push the steel plate to move and press the rubber to fix and seal the rock plate;

(4) rotating the fastening screws on the upper and lower sides until they comes into contact with the steel plate, recording the scale value S, and tightening the bolts until the scale is $w_o-w=S$, to make the fracture width value reaches the fracture width w designed in the experiment;

(5) using hexagon socket square bolts to fix the fluid inlet piston and the fluid outlet piston to the fluid inlet and fluid outlet of the box respectively to complete the installation of the plate holder.

In the present invention, the fluid inlet, fluid outlet and base on the left and right sides of the body of the rectangular box of the plate holder are tightly connected and sealed by seal rings, and then tightened by hexagon socket square bolts to ensure the tightness of the contact points between the base and the fluid inlet/outlet of the plate holder, and between the base and the fluid inlet/outlet piston, to prevent multiphase fluid leakage. Rock plate sample is placed in the inner cavity of the plate holder. The four sides of the rock plate, which are parallel to the flowing direction of multiphase fluid, are attached and covered with an equal area of anti-corrosion and anti-swelling rubber. The steel plate is pushed by the fastening screws of the plate holder to press the rubber and seal the sides of the rock plate, so as to ensure that the multiphase fluid only flows along the reserved fracture. All seal rings and rubber are made of corrosion-resistant and airtight materials, greatly slowing down the corrosion and swelling caused by corrosive fluids and high-penetrating gases in multiphase fluids to the seal rings. The upper part of the fastening screw is engraved with a scale with an accuracy of 1 mm to accurately measure the tightness of the bolt, which can realize the dynamic control of the sample fracture, ensure the controllability of the fracture in the simulation of multiphase fluid flow experiment, and ensure the diversity of rock plate samples in the holder. The plate holder is suitable for the simulation of the physicochemical effects of various multiphase fluids on the fractures of various rock materials.

The above are only the preferred embodiments of the present invention, and are not intended to limit the present invention in any form. Although the present invention has been disclosed as above with the preferred embodiments, it is not intended to limit the present invention. Those skilled in the art, within the scope of the technical solution of the present invention, can use the disclosed technical content to make a few changes or modify the equivalent embodiment with equivalent changes. Within the scope of the technical solution of the present invention, any simple modification, equivalent change and modification made to the above embodiments according to the technical essence of the present invention, are still regarded as a part of the technical solution of the present invention.

What is claimed is:

1. A plate holder for simulating flowing of multiphase fluids in fractures, comprising:
    a rectangular box, provided with a fluid inlet and a fluid outlet at left and right sides respectively, the fluid inlet is connected to a fluid inlet piston, the fluid outlet is connected to a fluid outlet piston, the fluid inlet piston and the fluid outlet piston are same in shape and structure, an internal flow channel of the fluid inlet piston is arranged as a first flared guide groove and an internal flow channel of the fluid outlet piston is arranged as a second flared guide groove, a flared end of the fluid inlet piston and a flared end of the fluid outlet piston are opposite to each other, and a cavity between the fluid inlet piston and the fluid outlet piston is a cuboid rock plate cavity; and
    a pair of horizontally-overlapped rectangular rock plates are installed in the cuboid rock plate cavity, a gap is between the two rock plates to simulate a fracture width, four sides parallel to a length direction of the rock plates are completely attached and covered with rubber, an outer side of the rubber is covered with steel plates, the rock plates is completely surrounded by the steel plates on four sides, fastening screws are installed vertically on the four sides of the rectangular box and directly opposite to the steel plates, screw ends are in contact with the steel plates, and the gap between the two rock plates is changed by-adjusting the fastening screws on an upper side and a lower side to simulate different fracture widths; the steel plates are pushed by adjusting the fastening screws on front and rear sides so as to press the rubber for sealing the sides of the rock plates; there are at least 2 fastening screws arranged on the upper and lower sides of a body of the rectangular box, and a scale for measuring length is provided on an upper part of the screw, with an accuracy of 1 mm; there are at least 4 fastening screws arranged on the front and rear sides; and all fastening screws are sleeved with seal rings.

2. The plate holder for simulating flowing of multiphase fluids in fractures according to claim 1, wherein the fluid inlet and the fluid outlet are arranged at centers of the left and right sides of the rectangular box respectively, bases are installed with hexagon socket square bolts respectively at the fluid inlet piston of the fluid inlet and the fluid outlet piston of the fluid outlet, a center of the base is provided with a fluid flow channel which is perpendicular to one side of the rectangular box, and the gap between the two plates is directly opposite to and connected with the fluid flow channel; an outer side of the base is installed with the fluid inlet piston of the fluid inlet or the fluid outlet piston of the fluid outlet by hexagon socket square bolts, flared ends of the fluid inlet piston and the fluid outlet piston are directly opposite to and connected with the fluid flow channel at the base center, and a shape and a size of the flared ends are same with the fluid flow channel of the base.

3. The plate holder for simulating flowing of multiphase fluids in fractures according to claim 2, wherein the base is composed of a base plate and a plug which is located at one side of the base plate and is vertically connected with the base plate, the base plate and the plug are integrally formed, the plug is inserted into the fluid inlet or the fluid outlet to completely block it, the base plate is located outside the rectangular box and tightly against the side of the box, the base plate and the side of the box are fixedly connected by hexagon socket square bolts, and an outer side of the base plate is connected with the fluid inlet piston or the fluid outlet piston by hexagon socket square bolts.

4. The plate holder for simulating flowing of multiphase fluids in fractures according to claim 3, wherein a seal ring is provided respectively at a contact position between the left and right sides of the rock plates and the plug, at a connection position between the left and right sides of the body of the rectangular box and the base plate, and at a connection position between the outer side of the base plate and the fluid inlet piston or the fluid outlet piston.

5. The plate holder for simulating flowing of multiphase fluids in fractures according to claim 1, wherein the left or right side of the body of the rectangular box is provided with a heater hole for inserting an electric heating rod.

6. The plate holder for simulating flowing of multiphase fluids in fractures according to claim 1, wherein the upper and lower sides of the body of the rectangular box are respectively provided with 3 fastening screws, which are located on a center line parallel to a long side of the body of the rectangular box and equally spaced.

7. The plate holder for simulating flowing of multiphase fluids in fractures according to claim 6, wherein the front and rear sides of the body of the rectangular box are respectively provided with 6 fastening screws, which are arranged in two rows, 3 screws in one row and equally spaced.

8. The plate holder for simulating flowing of multiphase fluids in fractures according to claim 7, wherein two sealing grooves are arranged at a lower part of all fastening screws, and seal rings are installed in the sealing grooves.

9. An operating method of the plate holder for simulating flowing of multiphase fluids in fractures according to claim 1, comprising the following steps:
    (1) preparing a pair of rectangular rock plates in line with a size of the rock plate cavity;
    (2) placing the pair of rock plates in a horizontally-overlapped way, with a spacing $w_o$ which is greater than the fracture width w designed for an experiment, attaching the rubber with the same area to the rock plates' four sides parallel to the internal flow channel, wrapping the four sides with the steel plates, and placing the wrapped rock plates horizontally in the rock plate cavity;
    (3) installing the fastening bolts vertically on the front and rear sides and the upper and lower sides of the plate holder box, which are directly opposite to the steel plates, and rotating and pushing the fastening bolts on the front and rear sides to push the steel plate to move and press the rubber to fix and seal the rock plates;
    (4) rotating the fastening bolts on the upper and lower sides until they comes into contact with the steel plate, recording the scale value S, and tightening the bolts until the scale is $w_o-w=S$, so as to make the fracture width value reaches the fracture width w designed in the experiment; and
    (5) using hexagon socket square bolts to fix the fluid inlet piston and the fluid outlet piston to the fluid inlet and fluid outlet of the rectangular box respectively to complete installation of the plate holder.

* * * * *